US011756649B2

(12) United States Patent
Gao et al.

(10) Patent No.: US 11,756,649 B2
(45) Date of Patent: Sep. 12, 2023

(54) SYSTEM, APPARATUS, AND METHOD FOR SEQUENCE-BASED ENZYME EC NUMBER PREDICTION BY DEEP LEARNING

(71) Applicant: KING ABDULLAH UNIVERSITY OF SCIENCE AND TECHNOLOGY, Thuwal (SA)

(72) Inventors: Xin Gao, Thuwal (SA); Yu Li, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 667 days.

(21) Appl. No.: 16/640,214

(22) PCT Filed: Oct. 16, 2018

(86) PCT No.: PCT/IB2018/058015
§ 371 (c)(1),
(2) Date: Feb. 19, 2020

(87) PCT Pub. No.: WO2019/077494
PCT Pub. Date: Apr. 25, 2019

(65) Prior Publication Data
US 2020/0365230 A1 Nov. 19, 2020

Related U.S. Application Data

(60) Provisional application No. 62/689,449, filed on Jun. 25, 2018, provisional application No. 62/572,658, filed on Oct. 16, 2017.

(51) Int. Cl.
*G16B 5/20* (2019.01)
*G06N 3/044* (2023.01)
(Continued)

(52) U.S. Cl.
CPC ............... *G16B 5/20* (2019.02); *G06N 3/044* (2023.01); *G06N 3/045* (2023.01); *G06N 3/08* (2013.01);
(Continued)

(58) Field of Classification Search
CPC .......... G16B 5/20; G16B 15/20; G16B 40/30; G16B 20/00; G06N 3/0445; G06N 3/0454;
(Continued)

(56) References Cited

U.S. PATENT DOCUMENTS

2003/0125548 A1* 7/2003 Arad .................... C07D 207/26
544/386
2013/0332133 A1* 12/2013 Horn ..................... G16B 50/00
703/11
2019/0220740 A1* 7/2019 Xiong .................... G16B 40/20

FOREIGN PATENT DOCUMENTS

WO   WO-2004099404 A2 * 11/2004   ............. G16B 20/00

OTHER PUBLICATIONS

Matsuta, Yoshihiko, Masahiro Ito, and Yukako Tohsato. "ECOH: an enzyme commission number predictor using mutual information and a support vector machine." Bioinformatics 29.3 (2013): 365-372. (Year: 2013).*

(Continued)

Primary Examiner — Jesse P Frumkin
(74) Attorney, Agent, or Firm — PATENT PORTFOLIO BUILDERS PLLC

(57) ABSTRACT

An apparatus, computer program product, and method are provided for the determination of one or more components of an EC number through the application of a level-by-level modeling approach capable of conducting feature reconstruction and classifier training simultaneously, based on encoded aspects of a sequence listing for a protein with an (Continued)

unknown function. The method includes receiving a sequence source data object associated with an enzyme; extracting a sequence data set from the sequence source data object; encoding the sequence data set into a first and second encoded sequence; generating a first predicted characteristic of the enzyme by applying the first and second encoded sequence to a first level of a model comprising a plurality of levels; and generating a second predicted characteristic of the enzyme by applying the first and the second encoded sequences to a second level of the model comprising a plurality of levels.

14 Claims, 5 Drawing Sheets

(51) Int. Cl.
    *G06N 3/045*     (2023.01)
    *G16B 20/00*     (2019.01)
    *G06N 3/08*     (2023.01)
    *G16B 15/20*     (2019.01)
    *G06N 3/084*     (2023.01)

(52) U.S. Cl.
    CPC .............. *G16B 15/20* (2019.02); *G16B 20/00* (2019.02); *G06N 3/084* (2013.01)

(58) Field of Classification Search
    CPC .......... G06N 3/08; G06N 3/084; G06N 3/044; G06N 3/045
    See application file for complete search history.

(56) References Cited

OTHER PUBLICATIONS

Wang, Tianmin, Hiroshi Mori, Chong Zhang, Ken Kurokawa, Xin-Hui Xing, and Takuji Yamada. "DomSign: a top-down annotation pipeline to enlarge enzyme space in the protein universe." BMC bioinformatics 16, No. 1 (2015): 1-15. (Year: 2015).*
Hamad, E. et al., "Neural Network Based Prediction of 3D Protein Structure as a Function of Enzyme Family Type and Amino Acid Sequences," JJBS Jordan Journal of Biological Sciences, Jun. 2017, vol. 10, No. 2, pp. 73-78.
International Search Report in related/corresponding International Application No. PCT/IB2018/058015, dated Apr. 9, 2019.
Li, Y. et al., "DEEPre: Sequence-Based Enzyme EC Number Prediction by Deep Learning," Bioinformatics, Oct. 23, 2017, vol. 34, No. 5, pp. 760-769, Oxford University Press.
Roy, A. et al., "A Benchmark Dataset for Fractured Reservoirs," Stanford University, 2012.
Volpato, V. et al., Accurate Prediction of Protein Enzymatic Class by N-to-1 Neural Networks, BMC Bioinformatics, Biomed Central, Jan. 14, 2002, vol. 14, Suppl. 1.
Written Opinion of the International Searching Authority in related/corresponding International Application No. PCT/IB2018/058015, dated Apr. 9, 2019.
Zacharaki, E.I. , "Prediction of Protein Function using a Deep Convolutional Neural Network Ensemble," PeerJ Computer Science, Jul. 17, 2017, vol. 3, 17 pp.

* cited by examiner

SYSTEM, APPARATUS, AND METHOD FOR SEQUENCE-BASED ENZYME EC NUMBER PREDICTION BY DEEP LEARNING

CROSS REFERENCE TO RELATED APPLICATIONS

This application is a U.S. National Stage Application of International Application No. PCT/IB2018/058015, filed on Oct. 16, 2018, which claims the benefit of U.S. Provisional Application No. 62/572,658 filed Oct. 16, 2017 and U.S. Provisional Application No. 62/689,449 filed Jun. 25, 2018, which are hereby incorporated by reference in their entirety.

TECHNOLOGICAL FIELD

Embodiments of the present invention relate generally to the automated prediction and modeling of enzyme function based on raw enzyme sequencing and the extraction of convolutional and sequential features.

BACKGROUND

Enzymes, an essential type of protein in the human body, play a vital role in catalyzing reactions in vivo and regulating biological processes. Enzyme function annotation has a broad range of applications in fields such as metagenomics, industrial biotechnology, and in the diagnosis of diseases caused by enzyme deficiencies. The dysfunction of certain enzymes is known to cause serious metabolic diseases. For example, the deficiency of alpha-galactosidase, which hydrolyses the terminal alpha-galactosyl moieties from glycolipids and glycoproteins, is believed to cause Fabry disease, resulting in full body pain, kidney insufficiency, and cardiac complications. The deficiency of DNA repair enzymes, which recognize and correct the physical damage in DNA, can cause the accumulation of mutations, which may further lead to various cancers. To investigate the causation of such diseases, which is an indispensable step in finding a way to cure them, it is crucial to understand the function of the related enzymes.

Conventionally, the investigation of enzyme function is conducted through experimental techniques, such as enzymatic assays. However, conducting experiments requires a significant amount of time and expert effort, which may not keep up with the rapid increase in the number of new enzymes. The inventors of the invention disclosed herein have identified these and other technical challenges present in the effective prediction of enzyme function, and have developed the solutions described and otherwise referenced herein.

BRIEF SUMMARY

An apparatus, computer program product, and method are therefore provided in accordance with an example embodiment in order permit the efficient classification of an enzyme and prediction of enzyme function based on enzyme sequence information. In this regard, the method, apparatus and computer program product of an example embodiment provide for the determination of one or more components of an EC number through the application of a level-by-level modeling approach capable of conducting feature reconstruction and classifier training simultaneously, based on encoded aspects of a sequence listing for a protein with an unknown function.

In one example embodiment, a method for predicting the function of an enzyme is provided, the method comprising: receiving a sequence source data object associated with an enzyme; extracting a sequence data set from the sequence source data object; encoding the sequence data set into a first encoded sequence and a second encoded sequence; generating a first predicted characteristic of the enzyme by applying the first encoded sequence and the second encoded sequence to a first level of a model comprising a plurality of levels; and generating a second predicted characteristic of the enzyme by applying the first encoded sequence and the second encoded sequence to a second level of the model comprising a plurality of levels.

In some example implementations of such a method, the first encoded sequence comprises a representation of a set of sequence-length dependent features of the enzyme. In some such example implementations, and in other example implementations, the second encoded sequence comprises a representation of a set of sequence-length independent features of the enzyme. In some such example implementations, and in other example implementations, applying the first encoded sequence and the second encoded sequence to a first level of a model comprising a plurality of levels comprises applying the first encoded sequence to a convolutional neural network components of the first level of the model. In some such example implementations, and in other example implementations, the method further involves applying an output of the convolutional neural network component to a recurrent neural network component of the first level of the model.

In some such example implementations, and in other example implementations, the first predicted characteristic is a first digit of an Enzyme Commission number associated with the enzyme and the second predicted characteristic is a second digit of the Enzyme Commission number associated with the enzyme. In some such example implementations, and in other example implementations, the method further involves generating a third predicted characteristic of the enzyme by applying the first encoded sequence and the second encoded sequence to a third level of a model comprising a plurality of levels; and generating a fourth predicted characteristic of the enzyme by applying the first encoded sequence and the second encoded sequence to a fourth level of the model comprising a plurality of levels.

In another example embodiment, an apparatus for predicting the function of an enzyme is provided, the apparatus comprising communications circuitry configured to receive a sequence source data object associated with an enzyme; processing circuitry configured to extract a sequence data set from the sequence source data object; sequence processing circuitry configured to encode the sequence data set into a first encoded sequence and a second encoded sequence; and enzyme function prediction circuitry configured to generate a first predicted characteristic of the enzyme by applying the first encoded sequence and the second encoded sequence to a first level of a model comprising a plurality of levels, wherein the enzyme function prediction circuitry is further configured to generate a second predicted characteristic of the enzyme by applying the first encoded sequence and the second encoded sequence to a second level of the model comprising a plurality of levels.

In some example implementations of such an apparatus, the first encoded sequence comprises a representation of a set of sequence-length dependent features of the enzyme. In some such example implementations, and in other example implementations, the second encoded sequence comprises a representation of a set of sequence-length independent features of the enzyme. In some such example implementations, and in other example implementations, the enzyme function prediction circuitry is configured to apply the first encoded sequence and the second encoded sequence to a first level of a model comprising a plurality of levels by at least applying the first encoded sequence to a convolutional neural network components of the first level of the model. In some such example implementations, and in other example implementations, the enzyme function prediction circuitry is further configured to apply an output of the convolutional neural network component to a recurrent neural network component of the first level of the model.

In some such example implementations, and in other example implementations, the first predicted characteristic is a first digit of an Enzyme Commission number associated with the enzyme and the second predicted characteristic is a second digit of the Enzyme Commission number associated with the enzyme. In some such example implementations, and in other example implementations, the enzyme function prediction circuitry is further configured to generate a third predicted characteristic of the enzyme by applying the first encoded sequence and the second encoded sequence to a third level of a model comprising a plurality of levels; and to generate a fourth predicted characteristic of the enzyme by applying the first encoded sequence and the second encoded sequence to a fourth level of the model comprising a plurality of levels.

In another example embodiment, a system for predicting the function of an enzyme is provided, the system comprising a plurality of models arranged in a plurality of levels, wherein the system is configured to: receive, via communications circuitry of an apparatus, a sequence source data object associated with an enzyme; extract, via processing circuitry of an apparatus, a sequence data set from the sequence source data object; encode the sequence data set into a first encoded sequence and a second encoded sequence; generate a first predicted characteristic of the enzyme by applying the first encoded sequence and the second encoded sequence to a first model at a first level of the system; and generate a second predicted characteristic of the enzyme by applying the first encoded sequence and the second encoded sequence to a second model at a second level of the system.

In some example implementations of such a system, the first encoded sequence comprises a representation of a set of sequence-length dependent features of the enzyme and wherein the second encoded sequence comprises a representation of a set of sequence-length independent features of the enzyme. In some such example implementations, and in other example implementations, applying the first encoded sequence and the second encoded sequence to the first model at the first level of the system comprises applying the first encoded sequence to a convolutional neural network components of the first model. In some such example implementations, and in other example implementations, applying the first encoded sequence and the second encoded sequence to the first model at the first level of the system further comprises applying an output of the convolutional neural network component to a recurrent neural network component of the first model.

In some such example implementations, and in other example implementations, the first predicted characteristic is a first digit of an Enzyme Commission number associated with the enzyme and the second predicted characteristic is a second digit of the Enzyme Commission number associated with the enzyme. In some such example implementations, and in other example implementations, the system is further configured to: generate a third predicted characteristic of the enzyme by applying the first encoded sequence and the second encoded sequence to a third model at a third level of the system; and generate a fourth predicted characteristic of the enzyme by applying the first encoded sequence and the second encoded sequence to a fourth model at a fourth level of the system.

BRIEF DESCRIPTION OF THE DRAWINGS

Figure 1:
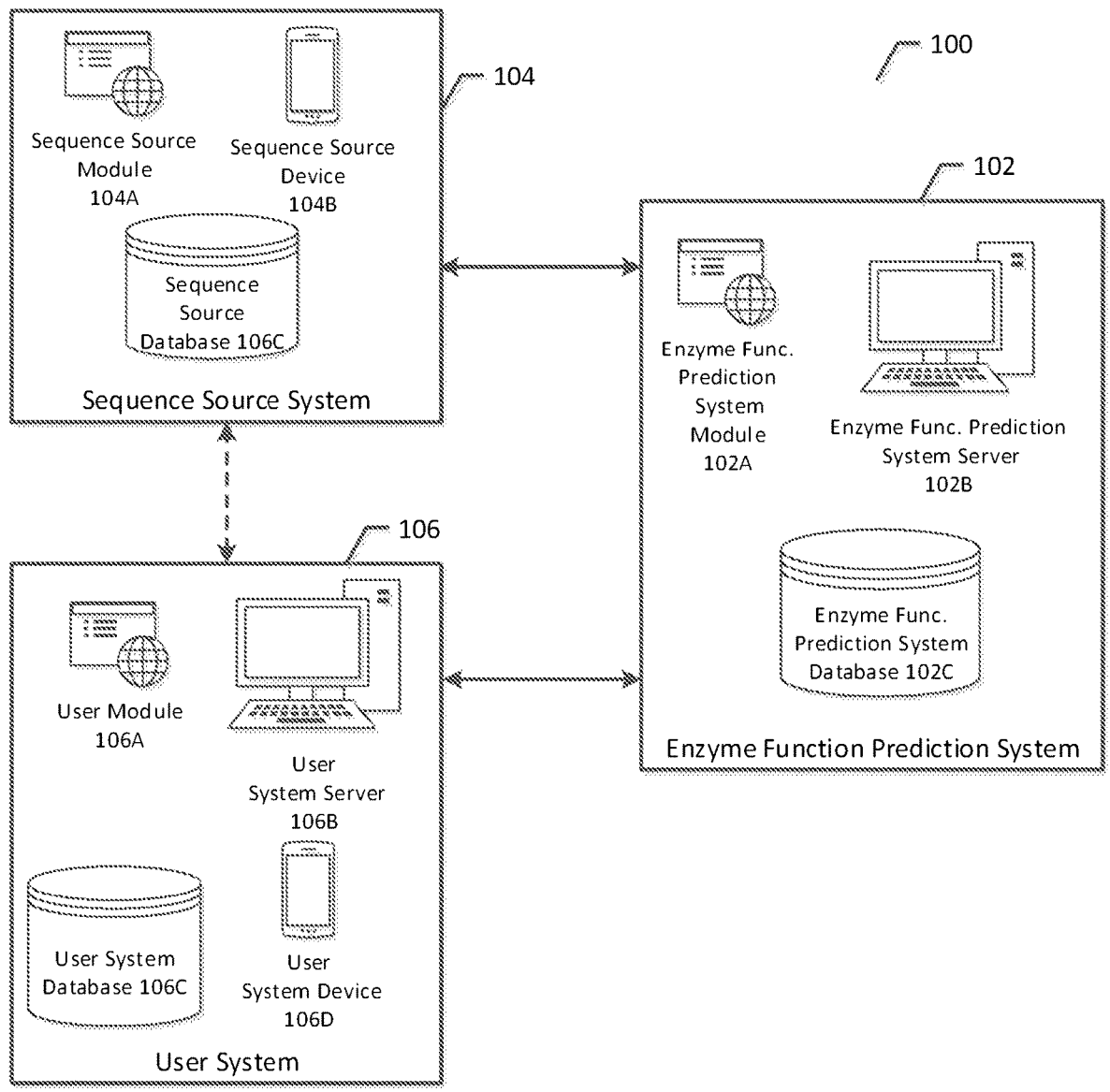
Figure 2:
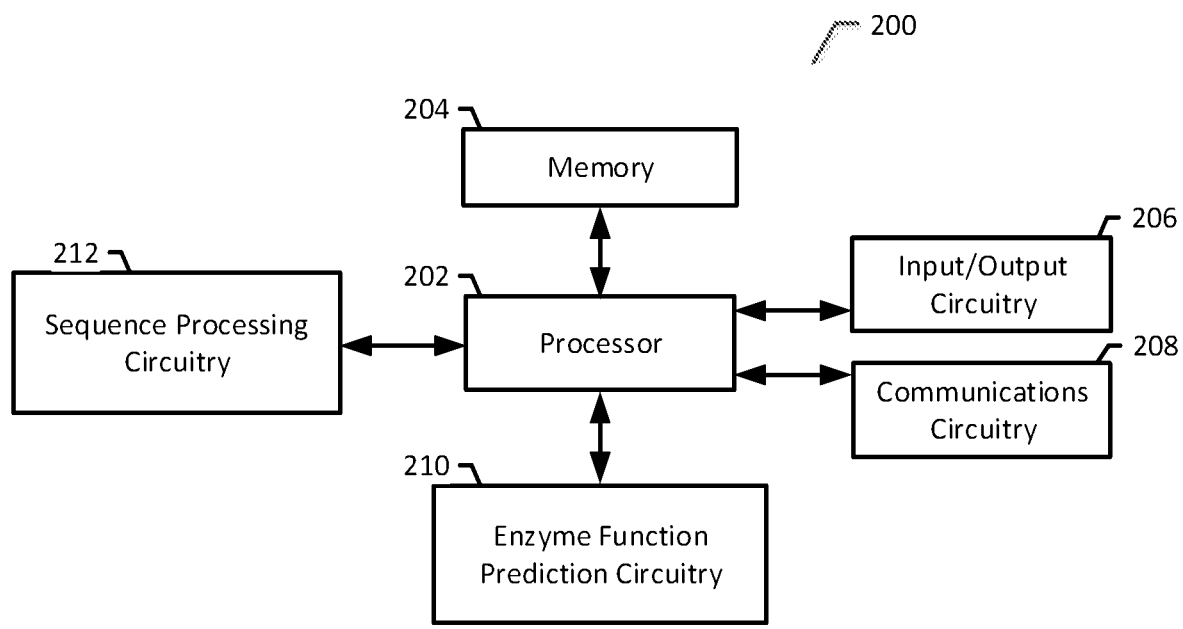
Figure 3:
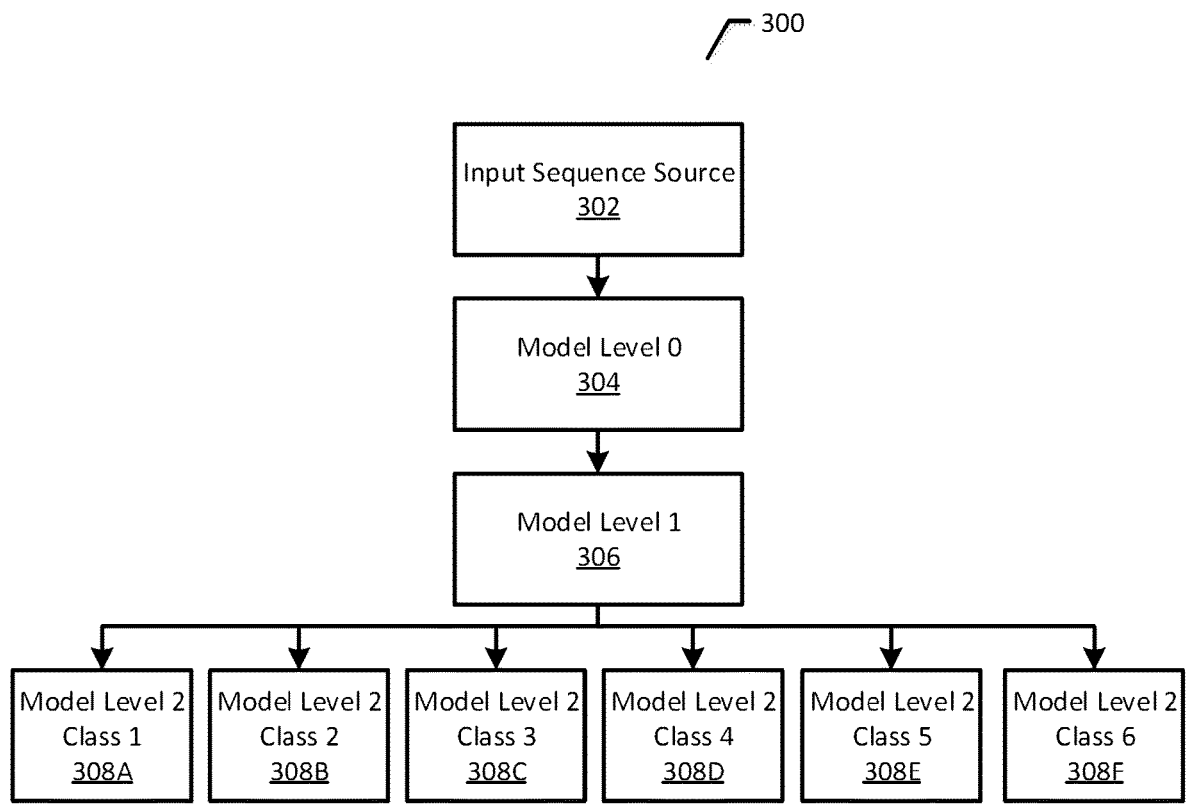
Figure 4:
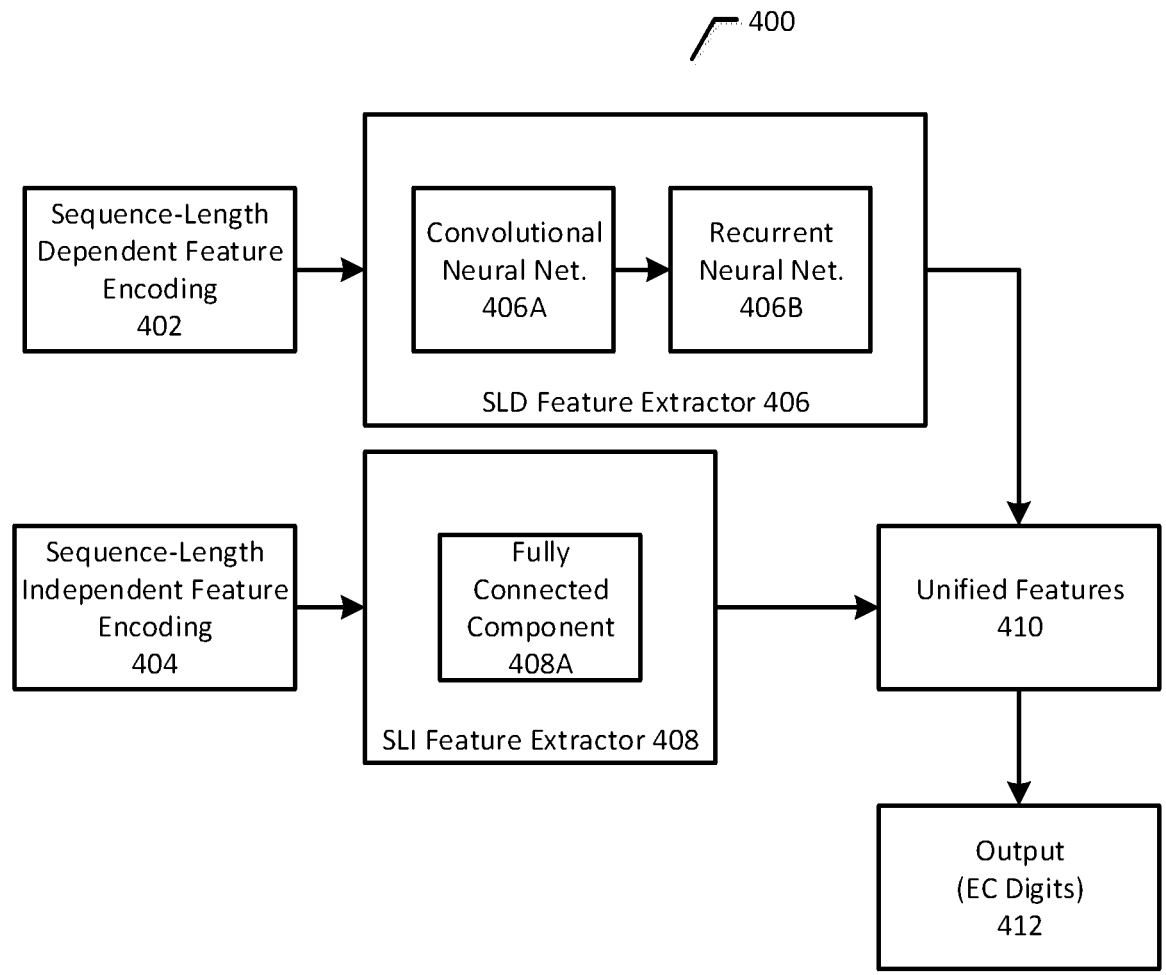
Figure 5:
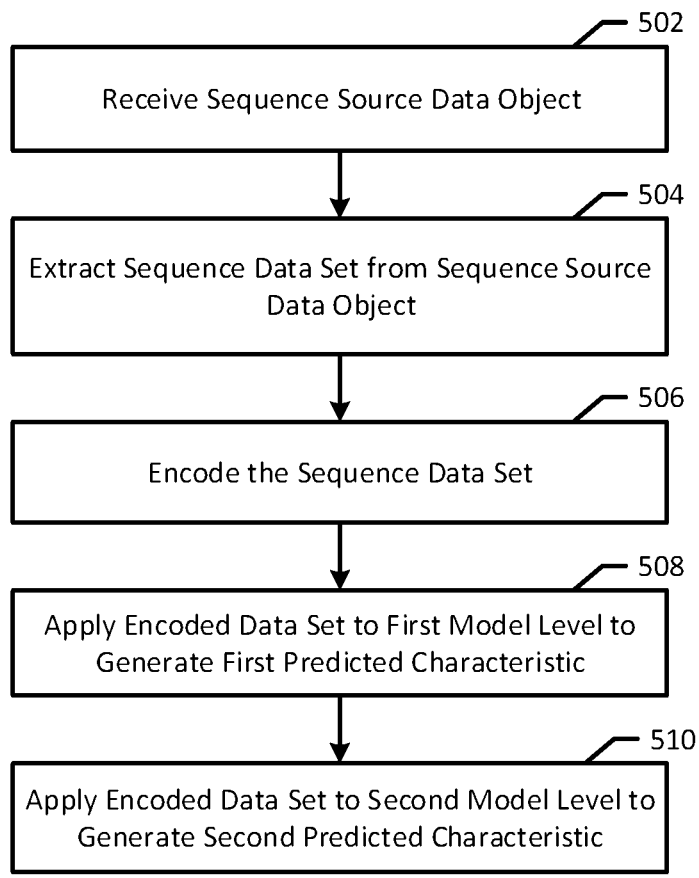

Having thus described certain embodiments of the present invention in general terms, reference will now be made to the accompanying drawings, which are not necessarily drawn to scale, and wherein:

FIG. 1 illustrates an example system within which some embodiments of the present invention may operate;

FIG. 2 illustrates a block diagram of an example device for implementing an enzyme function prediction system using special-purpose circuitry in accordance with some embodiments of the present invention;

FIG. 3 illustrates a block diagram depicting a functional overview of a level-by-level approach to predicting an enzyme's function in accordance with some embodiments of the present invention;

FIG. 4 illustrates a data flow model in accordance with some embodiments of the present invention; and FIG. 5 illustrates a flowchart describing example operations for generating resource allocations based on predicted conditions in accordance with some embodiments of the present invention.

DETAILED DESCRIPTION

Some embodiments of the present invention will now be described more fully herein with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. The term "or" is used herein in both the alternative and conjunctive sense, unless otherwise indicated. The terms "illustrative" and "exemplary" are used to be examples with no indication of quality level.

Technical and Contextual Overview

Computational tools that can predict the function of a protein, especially the detailed function of an enzyme, are essential for industrial biotechnology. Unlike the existing tools that manually extract designed features from the enzyme sequence or structure and predict enzyme function based on the manually-extracted features, an end-to-end enzyme function prediction pipeline is provided. Given an enzyme whose function is unknown, example embodiments of such a tool extract useful features, which are learned from the database by the tool itself without human interference, from the enzyme sequence and annotates the enzyme function automatically. In this regard, this tool is the first one that combines enzyme function prediction with deep learning and hierarchical classification.

The development of tools that perform enzyme function annotation is crucial for industrial biotechnology. In some example implementations, the tool described herein takes the sequence of the new enzyme as input, extracts tool self-learned features, and performs enzyme function prediction. This tool, only utilizing the sequence information to predict the detailed enzyme function, provides an initial functional check of newly discovered or newly designed enzymes, which are critical molecules in the biotechnology industry. By reducing the time and money spent on the design of a potentially unrelated enzyme, example embodiments of the tool described herein facilitate the development of new enzymes having specific functions, as well as designing a biosynthesis pathway.

As noted herein, the conventional approach to the investigation of enzyme function involves the use of experimental techniques, such as enzymatic assays. The significant amounts of time and expert effort necessary to conduct such experiments often impedes the ability of enzyme function investigations to keep up with the rapid increase in the number of new enzymes and the need for information regarding the likely function of identified enzymes. As such, conventional computational methods have emerged to assist biologists in determining enzyme function and guiding the direction of validating experiments.

Among the 539,566 manually annotated proteins, 258,733 proteins are enzymes. Such a large number of enzymes are usually classified using the Enzyme Commission (EC) system, the most well-known numerical enzyme classification scheme, which specifies the function of an enzyme by four digits. This classification system has a tree structure. After the root of the tree, there are two main nodes, standing for enzyme and non-enzyme proteins, respectively. Extending from the enzyme main node are six successor nodes, corresponding to the six main enzyme classes: (1) oxidoreductases, (2) transferases, (3) hydrolases, (4) lyases, (5) isomerases, and (6) ligases, represented by the first digit. Each main class node further extends out into several subclass nodes, specifying the enzyme's subclasses, represented by the second digit. With the same logic, the third digit indicates the enzyme's sub-subclasses and the fourth digit denotes the sub-sub-subclasses. By predicting the EC numbers precisely, computational methods can annotate the function of enzymes.

A number of computational methods have already been proposed to determine the enzyme function by predicting enzyme EC numbers. Firstly, because it is commonly believed that structures within the enzyme determine function, some research has focused on predicting the enzyme function by predicting the structure of the enzyme first. After obtaining the structure of an enzyme under study, a database or library (whose entries' EC numbers have already been determined and validated by experiments) is scanned, and the enzyme under study is assigned the EC number of the known enzyme or template with the most similar structure to the query. However, this sort of structure prediction is still relatively immature and time-consuming. Besides, since both the structure prediction step and the EC number prediction step can cause errors, the accumulated error through these steps tends to have a negative effect on the final prediction result. Secondly, the common assumption that enzymes with high sequence similarity tend to have similar functionality has led to research utilizing sequence similarity. Although this category of methods is widely used in practice, such methods are unable to make a prediction when encountering a sequence without significant homologies in the current databases. Thirdly, extracting features from the sequence and classifying the enzyme using machine learning algorithms has been, and remains, a studied direction. Although this direction has already been studied for over fifteen years with a number of software products and servers available, few of them combine the procedure of feature extraction and classification optimization together. Instead, previous studies rely heavily on manually-crafted features and consider feature extraction and classification as two separate problems. In spite of the success of such methods, with the rapid expansion of the known enzyme sequences, such manually-designed features are very likely to be a suboptimal feature representation which may be unsustainable in the omic era.

In addition to the technical difficulties described above, another issue in the protein general function prediction field is the feature dimensionality non-uniformity problem, which usually lies in the sequence-length-dependent features, such as PSSM (position-specific scoring matrix). For example, the dimensionality of PSSM can range from 50 by 20 to 5000 by 20, according to the corresponding sequence length. The feature uniformity requirement of mainstream classifiers has pushed out three strategies to this problem. Firstly, avoiding using the sequence-length-dependent features is the most straightforward solution to the problem. Although this approach can work under some certain circumstances, it eliminates the possibility of taking advantage of some powerful representation, such as PSSM, which can provide evolutional information. The second solution is to manually derive sequence-length-independent features from the sequence-length-dependent features. Pse-AAC (pseudo amino acid composition) and Pse-PSSM are typical examples of this category. The third solution is to systematically generate sequence-length-independent features, such as string kernels, which, however, do not consider the classification problem when extracting features. Despite the previous success of these three strategies, they still heavily depend on either manually-designed or pre-defined features, which are most likely to be suboptimal.

Accordingly, there exists a need for a more robust, automatic framework to extract problem-specific sequence-length-independent features from the sequence-length-dependent ones for dealing with the dimensionality problem. By providing a novel end-to-end approach to feature extraction and classifier training to predict enzyme function, example embodiments of the invention described herein meet this need.

Example System Environment

Turning now to the Figures, FIG. 1 shows an example system environment 100 in which implementations involving the efficient prediction of enzyme function may be realized. The depiction of environment 100 is not intended to limit or otherwise confine the embodiments described and contemplated herein to any particular configuration of elements or systems, nor is it intended to exclude any alternative configurations or systems for the set of configurations and systems that can be used in connection with embodiments of the present invention. Rather, FIG. 1 and the environment 100 disclosed therein is merely presented to provide an example basis and context for the facilitation of some of the features, aspects, and uses of the methods, apparatuses, and computer program products disclosed and contemplated herein. It will be understood that while many of the aspects and components presented in FIG. 1 are shown as discrete, separate elements, other configurations may be used in connection with the methods, apparatuses, and computer programs described herein, including configurations that combine, omit, and/or add aspects and/or components.

Embodiments implemented in a system environment such as system environment 100 advantageously provide for the prediction of enzyme function by applying encoded sequence data to models arranged in a level-by-level structure, where the models at each internal label node are configured to take into account sequence-length-dependent features and sequence-length-independent features while performing feature selection and classifier training simultaneously. Some such implementations contemplate the receipt and processing of sequence source data objects that contain a sequence for one or more enzymes to determine an EC number to apply to an otherwise unknown enzyme. Some such embodiments leverage a hardware and software arrangement or environment for the enzyme function prediction actions described, contemplated, and/or otherwise disclosed herein.

As shown in FIG. 1, an enzyme function prediction system 102 includes an online an enzyme function prediction system module 102A which is configured to receive, process, transform, transmit, communicate with, and evaluate sequence source data objects, the content and other information associated with such data objects, other data sets, and related interfaces via a web server, such as enzyme function prediction system server 102B and/or enzyme function prediction system device 102D. The enzyme function prediction system server 102B and/or enzyme function prediction system device 102D is connected to any of a number of public and/or private networks, including but not limited to the Internet, the public telephone network, and/or networks associated with particular communication systems or protocols, and may include at least one memory for storing at least application and communication programs.

It will be appreciated that all of the components shown in FIG. 1 may be configured to communicate over any wired or wireless communication network, including a wired or wireless local area network (LAN), personal area network (PAN), metropolitan area network (MAN), wide area network (WAN), or the like, as well as interface with any attendant hardware, software and/or firmware required to implement said networks (such as network routers and network switches, for example). For example, networks such as a cellular telephone, an 802.11, 802.16, 802.20 and/or WiMax network, as well as a public network, such as the Internet, a private network, such as an intranet, or combinations thereof, and any networking protocols now available or later developed including, but not limited to, TCP/IP based networking protocols may be used in connection with system environment 100 and embodiments of the invention that may be implemented therein or participate therein.

As shown in FIG. 1, enzyme function prediction system 102 also includes an enzyme function prediction database 102C that may be used to store information associated with sequence source data objects, users and/or other sources associated with sequence source data objects, other data sets, interfaces associated with any such data objects or data sets, sequence source systems, user systems, and/or any other information related to the prediction of the function of a given enzyme. The enzyme function prediction database 102C may be accessed by the enzyme function system module 102A and/or the enzyme function prediction system server 102B, and may be used to store any additional information accessed by and/or otherwise associated with the enzyme function prediction system 102 and/or its component parts. While FIG. 1 depicts enzyme function prediction system database 102C as a single structure, it will be appreciated that enzyme function prediction system database 102C may additionally or alternatively be implemented to allow for storage in a distributed fashion and/or at facilities that are physically remote from the each other and/or the other components of enzyme function prediction system 102.

Sequence source data objects, sequence information and/or additional content or other information to be associated with one or more sequence source data objects may originate from a sequence source system such as sequence source system 104. An operator of sequence source system 104 may use a sequence source device 104B, such as a laptop computer, desktop computer, or mobile device, for example, to interface with a sequence source module 104A to create, generate, and/or convey a sequence source data object and/or information to be included in a sequence source data object, such as a sequence associated with a potential enzyme and/or another sequence data set. The sequence source system 104 may (such as through the operation of the sequence source module 104A and/or the sequence source device 104B, for example) transmit a sequence source data object to the enzyme function prediction system 102. While only one sequence source system 104 is depicted in FIG. 1 in the interest of clarity, it will be appreciated that numerous other such systems may be present in system environment 100, permitting numerous users and/or sequence sources to develop and transmit sequence source data objects and/or information associated with sequence source data objects to enzyme prediction system 102.

As shown in FIG. 1, sequence source system 104 also includes a sequence source database 104C that may be used to store information associated with sequence source data objects, users and/or other sources associated with sequence source data objects, other data sets, interfaces associated with any such data objects or data sets, sequence source systems, user systems, and/or any other information related to the sequence associated with a potential enzyme and/or the prediction of the function of a given enzyme. The sequence source database 104C may be accessed by the sequence source module 104A, and/or the sequence source device 104B, and may be used to store any additional information accessed by and/or otherwise associated with the sequence source system 104 and/or its component parts. While FIG. 1 depicts sequence source database 104C as a single structure, it will be appreciated that sequence source prediction system database 104C may additionally or alternatively be implemented to allow for storage in a distributed fashion and/or at facilities that are physically remote from the each other and/or the other components of sequence source system 104.

As shown in FIG. 1, system environment 100 also includes user system 106, which comprises a user module 106A, a user system server 106B, a user system database 106C, and a user system device 106D. While only one user system 106 is depicted in FIG. 1 in the interest of clarity, it will be appreciated that numerous additional such systems may be present in system environment 100, permitting numerous users to communicate and/or otherwise interact with the enzyme function prediction system 102 and/or one or more sequence source systems 104. As shown in FIG. 1, the user system 106 is capable of communicating with enzyme function prediction system 102 to receive enzyme function information and/or to provide information that the enzyme function prediction system 102 may need when predicting the function and/or other characteristics of a given enzyme. For example, user system 106 may, such as via the capabilities and/or actions of the user system module 106A, user system server 106B, user system database 106C, and/or user system device 106D, obtain and provide information associated with a sequence associated with an enzyme of unknown classification or function, for example. In some instances the information received by the user system 106 may include a whole or partial EC number generated by the enzyme function prediction system 102.

User system 106 is also shown as including user system device 106D, which may take the form of a laptop computer, desktop computer, or mobile device, for example, to provide an additional means (other than via a user interface of the user system server 106B) to interface with the other components of user system 106 and/or other components shown in or otherwise contemplated by system environment 100.

User system 106 is also shown as optionally being capable of communicating with sequence source system 104. In some situations, such as when a given user system 106 is associated with a user engaged in a particular line of study with respect to certain potential enzymes, sequences, and/or applications of given enzymes or sequences, it may be advantageous for the user system 106 to interface with and/or otherwise be in communication with the sequence source system 104 in general and the sequence source device 104B in particular to enable a user to search, control, and/or otherwise interact with resources available from sequence source system 104.

Overall, and as depicted in system environment 100, enzyme function prediction system 102 engages in machine-to-machine communication with sequence source system 104 and user system 106, via one or more networks, to facilitate the processing of sequence source data objects received from a source of sequence information, the prediction of the function and/or classification of an enzyme associated with the sequence reflected in a sequence source data object, and the generation and/or transmission to a user of a representation of the function and/or classification of a given enzyme, such as an EC number, for example.

Example Apparatus for Implementing Embodiments of the Present Invention

It will be appreciated that the enzyme function prediction system 102 may be embodied by one or more computing systems, such as apparatus 200 shown in FIG. 2. As illustrated in FIG. 2, the apparatus 200 may include a processor 202, a memory 204, input/output circuitry 206, communications circuitry 208, enzyme function prediction circuitry 210, and sequence processing circuitry 212. The apparatus 200 may be configured to execute any of the operations described herein, including but not limited to those described in connection with FIG. 1, FIG. 3, FIG. 4, and FIG. 5.

Regardless of the manner in which the apparatus 200 is embodied, the apparatus of an example embodiment is configured to include or otherwise be in communication with a processor 202 and a memory device 204 and optionally the input/output circuitry 206 and/or a communications circuitry 208. In some embodiments, the processor (and/or co-processors or any other processing circuitry assisting or otherwise associated with the processor) may be in communication with the memory device via a bus for passing information among components of the apparatus. The memory device may be non-transitory and may include, for example, one or more volatile and/or non-volatile memories. In other words, for example, the memory device may be an electronic storage device (e.g., a computer readable storage medium) comprising gates configured to store data (e.g., bits) that may be retrievable by a machine (e.g., a computing device like the processor). The memory device may be configured to store information, data, content, applications, instructions, or the like for enabling the apparatus to carry out various functions in accordance with an example embodiment of the present invention. For example, the memory device could be configured to buffer input data for processing by the processor. Additionally or alternatively, the memory device could be configured to store instructions for execution by the processor.

As described above, the apparatus 200 may be embodied by a computing device. However, in some embodiments, the apparatus may be embodied as a chip or chip set. In other words, the apparatus may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The apparatus may therefore, in some cases, be configured to implement an embodiment of the present invention on a single chip or as a single "system on a chip." As such, in some cases, a chip or chipset may constitute means for performing one or more operations for providing the functionalities described herein.

The processor 202 may be embodied in a number of different ways. For example, the processor may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor may include one or more processing cores configured to perform independently. A multi-core processor may enable multiprocessing within a single physical package. Additionally or alternatively, the processor may include one or more processors configured in tandem via the bus to enable independent execution of instructions, pipelining and/or multithreading.

In an example embodiment, the processor 202 may be configured to execute instructions stored in the memory device 204 or otherwise accessible to the processor. Alternatively or additionally, the processor may be configured to execute hard coded functionality. As such, whether configured by hardware or software methods, or by a combination thereof, the processor may represent an entity (e.g., physically embodied in circuitry) capable of performing operations according to an embodiment of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform the algorithms and/or operations described herein when the instructions are executed. However, in some cases, the processor may be a processor of a specific device (e.g., a pass-through display or a mobile terminal) configured to employ an embodiment of the present invention by further configuration of the processor by instructions for performing the algorithms and/or operations described herein. The processor may include, among other things, a clock, an arithmetic logic unit (ALU) and logic gates configured to support operation of the processor.

In some embodiments, the apparatus 200 may optionally include input/output circuitry 206, such as a user interface that may, in turn, be in communication with the processor 202 to provide output to the user and, in some embodiments, to receive an indication of a user input. As such, the user interface may include a display and, in some embodiments, may also include a keyboard, a mouse, a joystick, a touch screen, touch areas, soft keys, a microphone, a speaker, or other input/output mechanisms. Alternatively or additionally, the processor may comprise user interface circuitry configured to control at least some functions of one or more user interface elements such as a display and, in some embodiments, a speaker, ringer, microphone and/or the like. The processor and/or user interface circuitry comprising the processor may be configured to control one or more functions of one or more user interface elements through computer program instructions (e.g., software and/or firmware) stored on a memory accessible to the processor (e.g., memory device 204, and/or the like).

The apparatus 200 may optionally also include the communication circuitry 208. The communication circuitry 208 may be any means such as a device or circuitry embodied in either hardware or a combination of hardware and software that is configured to receive and/or transmit data from/to a network and/or any other device or module in communication with the apparatus. In this regard, the communication interface may include, for example, an antenna (or multiple antennas) and supporting hardware and/or software for enabling communications with a wireless communication network. Additionally or alternatively, the communication interface may include the circuitry for interacting with the antenna(s) to cause transmission of signals via the antenna(s) or to handle receipt of signals received via the antenna(s). In some environments, the communication interface may alternatively or also support wired communication. As such, for example, the communication interface may include a communication modem and/or other hardware/software for supporting communication via cable, digital subscriber line (DSL), universal serial bus (USB) or other mechanisms.

As shown in FIG. 2, the apparatus may also include enzyme function prediction circuitry 210. The enzyme function prediction circuitry 210 includes hardware configured to maintain, manage, and provide access to a predictive model and/or information used by the predictive model to determine a predicted enzyme function associated with a given sequence. The enzyme function prediction circuitry 210 may provide an interface, such as an application programming interface (API), which allows other components of a system to obtain information associated with one or more enzymes and/or information associated with the likely function of an enzyme represented by a given input sequence. For example, the enzyme function prediction circuitry 210 may facilitate access to and/or processing of information regarding an enzyme's structure, its sequence-length-dependent features, its sequence-length-independent features, and/or other information that may be used to predict the function of an enzyme, including but not limited to any of the information that may be obtainable from and/or otherwise associated with a sequence source system 104 and/or a user system 106.

The enzyme function prediction circuitry 210 may facilitate access to encoded sequence information and/or other information used by the predictive model through the use of applications or APIs executed using a processor, such as the processor 202. However, it should also be appreciated that, in some embodiments, the enzyme function prediction circuitry 210 may include a separate processor, specially configured field programmable gate array (FPGA), or application specific interface circuit (ASIC) to manage the access and use of the relevant data. The enzyme function circuitry 210 may also provide interfaces allowing other components of the system to add or delete records to the enzyme function prediction system database 102C, and may also provide for communication with other components of the system and/or external systems via a network interface provided by the communications circuitry 208. The enzyme function prediction circuitry 210 may therefore be implemented using hardware components of the apparatus configured by either hardware or software for implementing these planned functions.

The sequence processing circuitry 212 includes hardware configured to manage, store, process, and analyze a sequence source data object, as well as the data sets and other information that may contained in and/or used to generate a sequence source data object. Because the information that may be accessed and used to create sequence source data objects may change frequently and/or be subject to control by other systems, it may be desirable to maintain a sequence source database separate from enzyme function database 102C and/or the memory 204 described above. It should also be appreciated though, that in some embodiments the enzyme function circuitry 210 and the sequence processing circuitry 212 may have similar and/or overlapping functionality. For example, both the enzyme function prediction circuitry 210 and the sequence processing circuitry 212 may interact with one or more data objects associated with a sequence to be evaluated, encoded portions of sequence information contained in such data objects, and/or other information associated with a sequence under evaluation. The sequence processing circuitry 212 may also provide access to other historical information, such as prior predictions, existing experimental data, and/or other research conducted with respect to a given sequence.

Aspects of Deep Learning and Hierarchical Classification

As used herein, the term "deep learning" refers generally to a popular machine learning method. Two main architectures associated with deep learning are applicable to addressing at least some of the particular technical challenges associated with bioinformatics environments: the convolutional neural network ("CNN") and the recurrent neural network ("RNN"). In some instances, these deep learning architectures have proven effective in addressing technical challenges associated with genetic analysis, sequence binding specificity prediction, and cryo-EM image processing.

Instead of being a pure classifier that depends on the manually-designed features such as SVM, CNN is considered to be an end-to-end wrapper classifier, at least in the sense that some CNN-based architectures are able to perform feature extraction based on the classification result and improve the performance of the machine learning model in a virtuous circle. As a complement to the capability of CNN-based architectures to capture significant features from a two-dimensional or three-dimensional matrix, RNN has the potential of encoding long-term interactions within the input sequence, which is usually a one-dimensional vector, such as the encoding of English words. In some example implementations of embodiments of the invention discussed and otherwise disclosed herein, the advantages of CNN and RNN are combined by using CNN to conduct feature extraction and dimensionality compression starting from the relevant raw two-dimensional encoding matrices, and by using RNN to extract the sequential, long-term interactions within the input sequence.

In overcoming some of the technical challenges associated with predicting the proper classification of an enzyme, example embodiments of the invention discussed and otherwise disclosed herein address aspects of enzyme function prediction as a classification problem with a tree structure in the label space, which can be viewed and treated as a hierarchical classification challenge. By viewing the prediction of the classification of an enzyme as both a multi-label classification challenge and as a multi-class classification challenge, three approaches to implementing a solution are possible: a flat classification approach, a local classifier approach, and a global classifier approach. Example implementations of embodiments of the invention disclosed and otherwise described herein reflect an advanced local classifier approach, at least in the sense that example implementations involve the construction of one classifier for each relevant internal node as part of the overall classification strategy.

Example Datasets

In some example implementations, including some example implementations aimed towards testing and validating approaches to some example embodiments of the advancements described herein, three datasets are used. However, it will be appreciated that some example implementations use and/or are otherwise capable of using other datasets in connection with predicting the classification of an enzyme. One dataset used in some example implementations was constructed from the ENZYME database, with a 40% sequence similarity cutoff. This dataset, referred to herein as "KNN" was released on or around May 1, 2007.

A second, larger dataset using more up-to-date databases was constructed by:

(1) Separating the SWISS-PROT database, which was released on or around Sep. 7, 2016 into enzymes and non-enzymes based on the annotation within the database;

(2) To attempt to guarantee uniqueness and correctness, excluding enzyme sequences with an incomplete EC number and/or more than one set of EC numbers;

(3) To attempt to avoid fragment data, excluding enzyme sequences annotated as "fragment", sequences with less than 50 amino acids, and sequences with more than 5000 amino acids;

(4) To attempt to remove a redundancy bias, using CD-HIT, with a 40% similarity threshold to sift upon the raw dataset, which resulted in 22,168 low-homology enzyme sequences; and (5) Constructing the non-enzyme portion of the data set by randomly collecting 22,168 non-enzyme protein sequences from the non-enzyme portion of the SWISS-PROT database, which were then subjected to steps 2, 3, and 4 above.

This second, larger dataset is referred to herein as the "NEW" dataset.

In some example implementations, the KNN dataset and the NEW dataset are used as benchmark datasets to evaluate the results of such example implementations through cross-fold validation. In order to test the generalization power of some example implementations of embodiments of the invention disclosed herein, one dataset can be used to train the relevant model, and a third dataset (which is independent of and non-overlapping with the training dataset) can be used to test the model, and thus avoid risks associated with overfitting. In some example implementations, this third dataset (used for cross-dataset validation) involved the benchmark dataset from Roy et al., 2012. This non-homologous dataset was collected from PDB and subjected to two requirements: (1) the pair-wise sequence similarity within the dataset must be below 30%, and (2) there is no self-BLAST hit within the dataset to ensure that there are no enzymes that are homologous to each other within the set. It will be appreciated that all enzymes this dataset have experimentally determined three-dimensional structures. To avoid overlaps between the training and testing datasets, sequences contained in both the training datasets and the third (testing) dataset were removed from the testing dataset, which reduced the size of the testing dataset to 284 enzyme sequences. The 284-sequence dataset is referred to herein as the COFACTOR dataset.

In the example implementations described herein, the KNN dataset contained 9,832 enzymes and 9,850 non-enzymes, the NEW dataset contained 22,168 enzymes and 22,168 non-enzymes, and the COFACTOR dataset contained 284 enzymes. However, it will be appreciated that datasets of different sources, sizes, and makeups can be used in example implementations.

Sequence Representation

Example implementations of the deep learning framework used in connection with example embodiments of the invention described herein overcome many of the technical challenges associated with predicting an enzyme classification by performing feature reconstruction and classifier training simultaneously. This approach eliminates the necessity of performing manual dimensionality uniformization processes and building complex, manually-designed features (which are unlikely to sustain the increasing volume and complexity of the relevant sequence data) within conventional systems.

In contrast to conventional systems, some example implementations of aspects of the deep learning framework described herein construct several features representing the relevant sequences directly from the input sequence. Based on the dimensionality of the input sequence, the features can be divided into two categories: sequence-length-dependent features and sequence-length-independent features. Some of these features include the following:

Sequence One-Hot Encoding:

One of the sequence-length-dependent features that can be derived directly from the input sequence is a one-hot encoding. To preserve the original sequence information, one-hot encoding is used in some example implementations as the first raw representation of the input sequence. In some such example implementations, the one-hot encoding uses one binary one and nineteen binary zeroes to represent each amino acid. For example, A is encoded as $(1, 0_1, \ldots 0_{19})$, while C is encoded as $(0_1, 1, \ldots 0_{19})$. For each input protein sequence, for example, the one-hot encoding can thus produce and L-by-20 matrix, where L represents the overall sequence length, with each row representing a specific spot and each column representing the appearance of a certain amino acid. For those sequences with an undetermined amino acid at a particular spot, a vector with twenty zeroes is used to represent that specific position.

Position Specific Scoring Matrix:

Another one of the sequence-length dependent features that can be derived directly from the input sequence is a position-specific scoring matrix. To provide the evolutional information to the training model, a position-specific scoring matrix (or PSSM) is deployed in some example implementations as a second sequence representation. In some such example implementations, the relevant PSSM is obtained through PSI-BLAST from BLAST+ with three iterations, with the E-value being 0.002 against the SWISS-PROT dataset.

Solvent Accessibility:

Another one of the sequence-length dependent features that can be derived directly from the input sequence is a solvent accessibility determination, which describes the openness of a local region of the enzyme. It will be appreciated that solvent accessibility is not directly available from a given database of enzyme sequences, and, in some example implementations, is predicted using DeepCNF. In some such example implementations, the protein sequence is taken as input into DeepCNF, which generates as output the possibilities of each amino acid of the sequence being in a buried, medium, or exposed state. In some such example implementations, thresholds are established between the buried, medium, and exposed states such that buried is defined as less than 10% accessibility, and exposed is defined as more than 40% accessibility, with the medium state accounting for the range between the thresholds. This encoding procedure produces an L-by-3 matrix, where L refers to the length of the relevant sequence.

Secondary Structure One-Hot Encoding:

Another one of the sequence-length dependent features that can be derived directly from the input sequence is a secondary structure one-hot encoding. In general, an amino acid can exist in one of three main secondary structure states: alpha-helix, beta-sheet, or random coil, which indicate the protein's local folding information. Similar to the approach taken with respect to solvent accessibility, Deep-CNF is used in some example implementations to predict the secondary structure of a given sequence, which results in an L-by-three matrix, wherein L refers to the length of the relevant sequence. In such a matrix, each row reflects the possibility of the amino acid folding into alpha-helix, beta-sheet, or random coil, respectively.

Functional Domain:

One of the sequence-length independent features that can be constructed directly from the input sequence is an identification of a relevant functional domain. It will be appreciated that, usually, a protein sequence contains one or several functional domains, which provide distinct functional and/or evolutionary information. For example, the Pfam database includes a collection of such functional domains, each of which may be represented by an HMM. By searching against the database, a functional domain encoding suitable for use in connection with the model described herein may be achieved by:

(1) For each protein sequence, using the HMMER searching engine in Pfam with an inclusion E-value of 0.01; and (2) Since the Pfam database includes 16,306 entries, employing a 16,306 dimensional vector to encode the searching result. In some such example implementations, if the i-th entry in the database is reported as a hit, a one is assigned to the corresponding position of the vector. Otherwise, a zero is assigned. Consequently, in such example implementations, the functional domain encoding of a protein sequence can be expressed as $F_{FUNCD}=[I_1, I_2, \ldots I_i, \ldots I_{16306}]$, where $I_i=1$, if the i-th entry in Pfam reported a hit, and 0 otherwise.

Aspects of the Classification Model

As noted herein, the challenge of effectively predicting an enzyme function can be viewed as a hierarchical classification challenge with a tree-structured label space. In some example implementations of embodiments of the invention disclosed herein, this challenge is overcome through the use of a level-by-level prediction framework through which a model is built for each internal label node. In such example implementations, the model features two main components: (1) a problem-specific feature extractor, which is configured to perform dimensionality uniformity and feature extraction, and (2) a classifier. As a novel, end-to-end model, the model disclosed herein is configured to perform feature selection and classifier training simultaneously in a virtuous circle, which results in the achievement of high performance by the model.

Level-by-Level Strategy:

As noted herein, the underlying data associated with enzyme function prediction, and other aspects of enzyme function prediction, impose numerous technical challenges. For example, the data set is relatively small (for example, 22,168 may be assigned to 58 classes until the second EC digit). Moreover, the relevant data often incorporates significant imbalances. For example, in the NEW dataset, 22,168 sequences relate to non-enzymes, while only ten sequences belong to subclass 1.20. To address these, and other technical challenges, some example implementations reflect a local classifier approach. In particular, such example implementations use a level-by-level prediction strategy.

FIG. 3 presents a depiction of a model system 300 that includes input sequence source 302 (such as sequence source system 104, for example) a group of models 304, 306, and 308A-308F arranged to implement a level-by-level strategy. For example, for a given sequence extracted from a sequence source data object received from input sequence source 302, the trained model system would first predict, at model level zero (indicated by block 304) whether the sequence is an enzyme or not. In instances where the sequence is predicted to be an enzyme, the model system 300 further proceeds to model level 1 (indicated by block 306) which predicts the first digit of the enzyme's EC number, which indicates the enzyme's main class. Upon knowing the main class, the model system 300 algorithmically chooses a trained model associated with the specific main class, and, through the application of the class-specific trained model, predicts the second digit of the enzyme's EC number, which is indicative of its subclass. As shown in FIG. 3, upon determining the main class, at model level 1 (block 306) one of the models at model level 2 (shown by blocks 308A-308F) that is associated with the determined class is used to further analyze the sequence information.

To reflect the label hierarchy associated with enzymes and their EC numbers, one model (shown as block 304) is built and trained to determine whether the input sequence is associated with an enzyme, one model (shown as block 306) is built and trained to determine the first digit of the EC number, and six models (shown as blocks 308A-308F) are built and trained to determine the second digit of the EC number. Likewise, corresponding numbers of models are built and trained for each successive EC number, depending on the number of subclasses and sub-subclasses to arrive (where sufficient data exists to reliably train the models associated with the fourth EC digit) at a whole and/or partial EC number. The use of a level-by-level approach allows the combined models to follow the structure of the EC number system.

In some example implementations, a convolutional neural network component is used to extract convolutional features, and a recurrent neural network component is used to extract sequential features from each sequence-length-dependent raw feature encoding. These features are then passed to a fully-connected component, which concatenates all extract features (including, for example, those that may be extracted from sequence-length-independent encoding) serves as the classifier.

Deep Neural Network Model:

As noted herein, at each prediction level, an end-to-end model is build based on a combination of deep neural network components. FIG. 4 presents a block diagram of such a model 400 which can be used in connection with example embodiments of the developments disclosed herein. As shown in FIG. 4, the model 400 is configured to accept encoded sequences that reflect sequence-length-dependent features of an enzyme (shown as block 402) and sequence-length-independent features of the enzyme (shown as block 404). With respect to the sequence-length-dependent features, such as PSSM for example, a sequence-length-dependent feature extractor 406, exploiting a convolutional neural network component 406A is used to extract convolutional features from the input map associated with the relevant sequence. Subsequently, a recurrent neural network component 406B configured with long short-term memory (LSTM) cells is used to extract sequential features from the output of the previous component (for example, the convolutional neural network component 406A. With respect to the sequence-length-independent feature or features, such as the functional domain encoding for example (which is a vector), sequence-length-independent feature extractor 408, which incorporates a fully-connected component 408A is used to perform dimensionality reduction and feature extraction. A second fully-connected component 410 is configured to unify the features extracted by the sequence-length-dependent feature extractor 406 and the sequence-length-independent feature extractor 408 is used to combine the extracted pieces of information, which are then fed to a softmax layer component 412 for classification, which may, in some example implementations, result in the output of one or more EC digits.

The model structure shown in FIG. 4 may be particularly advantageous when multiple instances of the model 400 are structured in the layered arrangement shown in FIG. 3, as each model instance may be trained to process the encoded sequences representing the sequence-length-dependent and sequence-length independent features of a given sequences under investigation in a manner that focuses the given model instance on the classification relevant to its particular location in the layered structure. As noted herein, it is possible to treat at least some of the technical challenges associated with a given as a tree-based classification problem reflecting the classification structure established by the Enzyme Commission numbering system. As such, instead of requiring a given model component to be capable of fully assessing a sequence in a single step, the layer-by-layer approach reflected in FIG. 3 allows multiple instances of models (such as the model 400) to be purposefully built and trained to fulfill their respective roles within the structure.

For example, an instance of model 400 in FIG. 4 may be arranged to be located to determine a subclass of a given enzyme, such as in position 308A of FIG. 3. Upon receiving an encoded sequence representing sequence-length-dependent features from block 402, the sequence-length-dependent feature extractor 406 first applies the encoded sequence to the convolutional neural network 406A, the output of which is applied to the recurrent neural network component 406B. Similarly, the encoded sequence representing one or more sequence-length-independent features of the enzyme are applied to the fully connected component 408A in the sequence-length-independent feature extractor 408. The output of feature extractors 406 and 406 are then combined and unified at the fully connected component 410, and the unified features are passed to the softmax layer component 412, where a predicted characteristic (such as an EC number associated with a given subclass, for example) is determined. Since each instance of the model 400 is known to be in a given location within the layer-by-layer structure, the individual model instances (and their respective components, for example) may be trained in light of their position within the layered structure. For example, if a model instance is positioned to determine a particular subclass of an enzyme, it is, in some example implementations, positioned such that the class of the enzyme is already known or predicted. As such, the particular model instance need not be trained to re-determine the relevant class of the enzyme, and likewise need not be trained to identify subclasses that are not relevant to its associated class.

In some example embodiments, during training of the model and/or model components, the training error is back-propagated to each component. As a result, the back-propagated error guides the convolutional neural network component and the recurrent neural network component to perform an end-to-end feature selection, weighing more on the features which would improve the final performance while weighing less on unimportant features automatically. At the same time, the weights of other components may be adjusted simultaneously or near-simultaneously to adopt the change. By coupling the effect of feature extraction and classifier training, the performance of the model can be optimized and/or otherwise improved.

In order to overcome the risks of overfitting the model that are present in situations that use a highly complex and flexible model, some example implementations incorporate one or more approaches to limit the potential for overfitting. For example, a weight decay approach may be taken to counteract the tendency for a deep neural network model to reproduce the detail of noise (which is usually non-smooth), by applying extreme weights. By modifying the relevant objective function by adding an L-2 norm term of weights, the probability of arriving at extreme weights (which can manifest as an overfitting issue), can be reduced.

Another approach to avoiding or limiting the effects of overweighting involves a dropout approach. A dropout approach typically involves randomly dropping nodes during training, which prevents the dropped nodes from co-adapting too much, reduces the complexity of the model, and preserves the model power. A third approach used in some example implementations involves batch normalization, which extends the concept of data normalization and is typically performed during data processing. In some example implementations, due to the availability of weight and parameter adjustments, the input of the internal layers of the mode may be too large or too small (which is referred to as internal covariate shift), resulting in a situation where preprocessing normalization becomes meaningless. To overcome this technical issue, in addition to normalizing the data prior to its application to the model, the input to each internal layer is normalized. In addition to reducing the risks associated with overfitting, the batch normalization approach also reduces the heavy dependency of knowledge-intensive initialization when training the model to allow a larger learning rate when tuning the model.

In some example implementations, an adaptive moment estimation approach may be used to as the optimizer when developing the relevant model. As an improved version of approaches rooted in stochastic gradient descent techniques, such an approach tends to minimize weighted cross entropy loss. In some such example implementations, class imbalances within the training data set were handled by re-scaling predictions of each class by its respective weight. For example, instead of setting the learning rate as a hyperparameter manually as in stochastic gradient descent and momentum, the approach taken in some example implementations computes the adaptive learning rate for each individual parameter by estimating the first and second movement of the gradients at the cost of computational time and memory. Such an optimizer approach combines the advantage of RMSprop, which computes the adaptive learning rate at each step, and momentum, which reduces the oscillation problem of stochastic gradient descent by making the weight update considering both the gradient and the update of the previous step.

In some example implementations, when training the second-digit predictive models, a transfer learning-like approach is taken. Since the available training datasets are limited, and further divided into six parts (corresponding with each of the six main enzyme classes), the amount of data belonging to each main class is, in some instances, insufficient to produce a model with the ability to extract features and being generalized well. To overcome this technical challenge imposed by limited training data, the relevant convolutional neural network component and the recurrent neural network component of the relevant model are, in some example implementations, pre-trained by using all of the training data. Subsequently, for training each second-digit prediction model, the parameters of the CNN and RNN components of the model are fixed, and fine tuning is only applied to the fully connected components using the specific subset of the training data relevant to that digit.

FIG. 5 depicts a block diagram of an example process flow 500 that may be followed by an example apparatus, such as the apparatus 200, for example, to implement aspects of embodiments of the developments described herein. Overall, as shown in FIG. 5, an apparatus in accordance with example embodiments of the invention includes means, such as processor 202, memory 204, input/output circuitry 206, communications circuitry 208, enzyme function prediction circuitry 210, and sequence processing circuitry 212 to receive a sequence source data object associated with an enzyme, extract a sequence data set from the sequence source data object, encode the sequence data set, and apply the encoded sequence data set to models arranged in a multi-layered structure to generate predicted characteristics of the enzyme reflected by the sequence contained in the sequence source data object.

As shown in FIG. 5, the process 500 commences at block 502, which comprises receiving a sequence source data object associated with an enzyme. In some example implementations, the apparatus 200, such as via input/output circuitry 206 and/or communications circuitry 208, receives a sequence source data object. In some such example implementations, the sequence source data object is received, either directly, or indirectly, from a sequence source system, such as sequence source system 104 discussed herein in connection with FIG. 1. The received sequence source data object contains at least a sequence data set, which may take the form of a sequence listing associated with an enzyme and/or another indication of a sequence to be used in connection with predicting the functionality of a given enzyme. In some example implementations, the sequence source data object may incorporate additional data and/or metadata regarding a relevant sequence, user, and/or prediction of the functions of a given enzyme sequence.

As shown in FIG. 5, the process 500 continues at block 506, which involves extracting the sequence data set from the sequence source data object. In some example implementations, the apparatus 200, such as via the processor 202, memory 204, and/or sequence processing circuitry 212 may extract all and/or a portion of the data incorporated into a sequence source data object to form a sequence data set. In some example implementations, and as discussed herein, the sequence data set may reflect and/or incorporate a raw sequence obtained from one or more databases.

As shown in FIG. 5, the process 500 continues at block 506, which includes encoding the sequence data set into a first encoded sequence and a second encoded sequence. In some example implementations, the apparatus 200, such as via the processor 200, memory 204 and/or sequence processing circuitry 212 may encode the extracted sequence data set in advance of applying the sequence data set to one or more models. In some such example implementations, at least a first encoded sequence and a second encoded sequence are formed from by encoding the sequence data set. For example, the first encoded sequence may comprise a representation of a set of sequence-length-dependent features of the enzyme, while the second encoded sequence may comprise a representation of a set of sequence-length-independent features of the enzyme. It will be appreciated that any of the approaches to encoding a sequence discussed herein, including but not limited to sequence one-hot encoding, PSSM encoding, solvent accessibility encoding, secondary structure one-hot encoding, and/or functional domain encoding may be used in connection with example implementations of block 506.

As shown in FIG. 5, the process 500 continues at block 508, which includes generating a first predicted characteristic of the enzyme by applying the first encoded sequence and the second encoded sequence to a first level of a model comprising a plurality of levels. As discussed herein, such as in connection with FIGS. 3 and 4, some example implementations of embodiments of the invention use a layer-by-layer approach to constructing a model that reflects the tree structure of the EC numbering system for classifying enzymes. As such, in some example implementations, the apparatus 200, such as via the processor 200, memory 204 and/or enzyme function prediction circuitry 210 may apply the encoded sequences to a first level of a model to generate a first predicted characteristic, such as a first digit of an EC number, for example. In some example implementations, such as those that involve model structures similar to that shown in FIG. 4, applying the first encoded sequence and the second encoded sequence to a first level of a model comprising a plurality of levels involves applying the first encoded sequence (such as an encoded sequence that includes a representation of sequence-length-dependent features, for example) to a convolutional neural network component of a model. In some such example implementations, the output of the convolutional neural network component of the model may be further applied to a recurrent neural network component of the same model.

As shown in FIG. 5, the process continues at block 510, which includes generating a second predicted characteristic of the enzyme by applying the first encoded sequence and the second encoded sequence to a second level of a model comprising a plurality of levels. As with example implementations, of block 508, the apparatus 200, such as via the processor 200, memory 204 and/or enzyme function prediction circuitry 210 may apply the encoded sequences to a second level of a model to generate a second predicted characteristic, such as a second digit of an EC number, for example. As discussed herein, such as in connection with FIGS. 3 and 4, for example, a model (such as the example model 400, for example) may be implemented at each node of the layered, tree-like structure used to evaluate a sequence under investigation. As such, after a first EC digit, classification, or other characteristic is determined, the encoded sequence information may be passed to the next level of the model to generate a second EC digit, sub-classification, or other characteristic of the enzyme. In some instances, such as where a user seeks to generate a whole and/or partial EC number for a sequence under investigation, the process 500 may be extended to include generating a third predicted characteristic of the enzyme (such as a third EC digit, for example) by applying the first and second encoded sequences to a third level of the model. Likewise, to generate a fourth EC digit or other predicted characteristic, the first and second encoded sequences may be applied to a fourth level of the model. In some example implementations where multiple nodes of the layered structure feature models similar to the example model 400 and/or other models, the first encoded sequence is applied to a convolutional neural network, the output of which may be further applied to a recurrent neural network, as discussed herein.

Selected Example Implementations

As discussed herein, the prediction of enzyme function may be particularly advantageous in situations and contexts involving the study of the function of enzymes involved in in vivo reactions. One such example situation in which an example implementation of the developments described herein are advantageous involves the study of glutaminase. Glutaminase is a phosphate-activated enzyme, which catalyzes the first step of glutaminolysis, hydrolyzing glutamine into glutamate. The alternative splicing of its messenger RNA results in its three isoforms, with isoform 1 and isoform 3 being capable of catalyzing while isoform 2 lacks catalytic ability. In an example implementation of an embodiment of the developments described herein, sequences of the three glutaminase isoforms were obtained and applied to an example model with a structure similar to that presented in connection with FIGS. 3 and 4. The model predicted that isoform 1 and isoform 3 of glutaminase were hydrolases acting on carbon-nitrogen bonds, in a manner consistent with experimental results. Moreover, the model successfully recognized isoform 2, which experimental results indicate lacks catalytic ability, as a non-enzyme.

Another example implementation involved an analysis of aurora kinases B, which is a key enzyme in the regulation of chromosomal segregation during mitosis, ensuring correct chromosome alignment and segregation, as well as chromatin-induced microtubule stabilization and spindle assembly. It is believed that over-expression of aurora kinases B possibly causes unequal distribution of genetic information, which may result in aneuploid cells, which may become cancerous. Aurora kinases B has five isoforms that result from alternative splicing. Four of the isoforms have roughly equal lengths with high similarity, while isoform 3, which has high expression in the metastatic liver with no expression in the normal liver, is only half of the length of the "canonical" isoform (142 amino acids, as opposed to 344 amino acids). Despite its much shorter length, the isoform does not lose its functionality. In an example implementation of an embodiment of the developments described herein, sequences of the five isoforms were obtained and applied to an example model with a structure similar to that presented in connection with FIGS. 3 and 4. The model successfully predicted characteristics of all five isoforms consistent with the known experimental results, including the successful prediction of isoform 3's functionality, notwithstanding its shorter sequence length.

It will be appreciated that, while some of the example implementations presented herein reflect contexts and/or other situations involving a uni-functional enzyme (and/or such contexts or situations where an assumption that a given enzyme is uni-functional, for example), some example implementations of embodiments of the invention may be used with multi-functional and/or potentially multi-functional enzymes. In many situations, the assumption that an enzyme is uni-functional in the sense that it can only catalyze one kind of biochemical reaction is appropriate. However, approximately five thousand multi-functional enzymes are known to exist, and it is possible that example implementations of embodiments of the invention described and/or otherwise disclosed herein may encounter previously untested enzymes that may be multi-functional.

The flexible framework exhibited by many example implementations of embodiments of the invention described herein is particularly advantageous in addressing the technical challenges associated with identifying and classifying multi-functional enzymes. In particular, the hierarchical classification strategy reflected in some example implementations allows for a determination to be made (such as by one or more of the models described herein, for example) predicting whether or not a given sequence under examination is likely to be a multi-functional enzyme. Upon determining whether a given enzyme is a multi-functional enzyme, example implementations of the models described and/or otherwise disclosed herein may be used to determine the four-digit detailed annotation for each function of the multi-functional enzyme. Since such example implementations effectively leverage a constructed, model to determine multiple different four-digit annotations for multiple functions of a single enzyme, the overhead associated with building one or more separate systems to handle multi-functional enzymes (as opposed to uni-functional enzymes, for example), can be avoided.

In some example implementations involving multi-functional enzymes, many of the technical challenges associated with classifying a multi-functional enzyme can be overcome by using the model and/or its related components to determine and/or otherwise obtain the main classes for a potentially multi-functional enzyme. In one set of example implementations, obtaining the main classes for a potentially multi-functional enzyme can be treated as a multi-label classification challenge. For example, one or more models may be constructed to reflect an approach using a neural network to perform a multi-label classification (such as a BP-MLL-based approach, for example) may be used. In some such example using a BP-MLL-based approach, the loss function of a typical neural network is modified into a specific loss to rank the labels belonging to the instance higher than those labels not belonging to the instance. Such approaches may be further extended through the application of one or more deep learning approaches to BP-MLL-based protocols, for example.

Additional Implementation Details

Although an example processing system has been described in FIG. 2, implementations of the subject matter and the functional operations described herein can be implemented in other types of digital electronic circuitry, or in computer software, firmware, or hardware, including the structures disclosed in this specification and their structural equivalents, or in combinations of one or more of them.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more modules of computer program instructions, encoded on computer storage medium for execution by, or to control the operation of, information/data processing apparatus. Alternatively, or in addition, the program instructions can be encoded on an artificially-generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or information/data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input information/data and generating output. Processors suitable for the execution of a computer program include, by way of example, both general and special purpose microprocessors, and any one or more processors of any kind of digital computer. Generally, a processor will receive instructions and information/data from a read-only memory or a random access memory or both. The essential elements of a computer are a processor for performing actions in accordance with instructions and one or more memory devices for storing instructions and data. Generally, a computer will also include, or be operatively coupled to receive information/data from or transfer information/data to, or both, one or more mass storage devices for storing data, e.g., magnetic, magneto-optical disks, or optical disks. However, a computer need not have such devices. Devices suitable for storing computer program instructions and information/data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described herein can be implemented on a computer having a display device, e.g., a CRT (cathode ray tube) or LCD (liquid crystal display) monitor, for displaying information/data to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described herein can be implemented in a computing system that includes a back-end component, e.g., as an information/data server, or that includes a middleware component, e.g., an application server, or that includes a front-end component, e.g., a client computer having a graphical user interface or a web browser through which a user can interact with an implementation of the subject matter described herein, or any combination of one or more such back-end, middleware, or front-end components. The components of the system can be interconnected by any form or medium of digital information/data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits information/data (e.g., an HTML page) to a client device (e.g., for purposes of displaying information/data to and receiving user input from a user interacting with the client device). Information/data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of particular inventions. Certain features that are described herein in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. Many modifications and other embodiments of the inventions set forth herein will come to mind to one skilled in the art to which the inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for predicting the function of an enzyme, the method comprising:
   receiving a sequence source data object associated with an enzyme;
   extracting a sequence data set from the sequence source data object;
   encoding the sequence data set into a first encoded sequence and a second encoded sequence;
   generating a first predicted characteristic of the enzyme by applying the first encoded sequence and the second encoded sequence to a first level of a model system comprising a plurality of levels, wherein the first encoded sequence is applied to a convolutional neural network component of the first level of the model system, and an output of the convolutional neural network component is applied to a recurrent neural network component of the first level of the model system; and
   generating a second predicted characteristic of the enzyme by applying the first encoded sequence and the second encoded sequence to a second level of the model system comprising a plurality of levels,
   wherein a first model of the first level generates a first digit that corresponds to a class of the enzyme, and a second model of the second level is selected based on the class, and generates a second digit that corresponds to a subclass of the enzyme, with the second model being one of six models of the second level, and
   wherein the first model is trained to determine the class and the six models are trained to determine the subclass.

2. The method of claim 1, wherein the first encoded sequence comprises a representation of a set of sequence-length dependent features of the enzyme.

3. The method of claim 1, wherein the second encoded sequence comprises a representation of a set of sequence-length independent features of the enzyme.

4. The method of claim 1, wherein the first predicted characteristic is the first digit of an Enzyme Commission number associated with the enzyme and the second predicted characteristic is the second digit of the Enzyme Commission number associated with the enzyme.

5. The method of claim 1 further comprising:
   generating a third predicted characteristic of the enzyme by applying the first encoded sequence and the second encoded sequence to a third level of the model system comprising a plurality of levels; and
   generating a fourth predicted characteristic of the enzyme by applying the first encoded sequence and the second encoded sequence to a fourth level of the model system comprising a plurality of levels.

6. An apparatus for predicting the function of an enzyme, the apparatus comprising:
   communications circuitry configured to receive a sequence source data object associated with an enzyme;
   processing circuitry configured to extract a sequence data set from the sequence source data object;
   sequence processing circuitry configured to encode the sequence data set into a first encoded sequence and a second encoded sequence;

enzyme function prediction circuitry configured to generate a first predicted characteristic of the enzyme by applying the first encoded sequence and the second encoded sequence to a first level of a model system comprising a plurality of levels, wherein the first encoded sequence is applied to a convolutional neural network component of the first level of the model system, and an output of the convolutional neural network component is applied to a recurrent neural network component of the first level of the model system, and wherein the enzyme function prediction circuitry is further configured to generate a second predicted characteristic of the enzyme by applying the first encoded sequence and the second encoded sequence to a second level of the model system comprising a plurality of levels, wherein a first model of the first level generates a first digit that corresponds to a class of the enzyme, and a second model of the second level is selected based on the class, and generates a second digit that corresponds to a subclass of the enzyme, with the second model being one of six models of the second level, and wherein the first model is trained to determine the class and the six models are trained to determine the subclass.

7. The apparatus of claim 6, wherein the first encoded sequence comprises a representation of a set of sequence-length dependent features of the enzyme.

8. The apparatus of claim 6, wherein the second encoded sequence comprises a representation of a set of sequence-length independent features of the enzyme.

9. The apparatus of claim 6, wherein the first predicted characteristic is the first digit of an Enzyme Commission number associated with the enzyme and the second predicted characteristic is the second digit of the Enzyme Commission number associated with the enzyme.

10. The apparatus of claim 6, wherein the enzyme function prediction circuitry is further configured to:
generate a third predicted characteristic of the enzyme by applying the first encoded sequence and the second encoded sequence to a third level of the model system comprising a plurality of levels; and
generate a fourth predicted characteristic of the enzyme by applying the first encoded sequence and the second encoded sequence to a fourth level of the model system comprising a plurality of levels.

11. A system for predicting the function of an enzyme, the system comprising a plurality of models arranged in a plurality of levels, wherein the system is configured to:

receive, via communications circuitry of an apparatus, a sequence source data object associated with an enzyme;
extract, via processing circuitry of an apparatus, a sequence data set from the sequence source data object;
encode the sequence data set into a first encoded sequence and a second encoded sequence;
generate a first predicted characteristic of the enzyme by applying the first encoded sequence and the second encoded sequence to a first model at a first level of the system, wherein the first encoded sequence is applied to a convolutional neural network component of the first level of the model system, and an output of the convolutional neural network component is applied to a recurrent neural network component of the first level of the model system; and
generate a second predicted characteristic of the enzyme by applying the first encoded sequence and the second encoded sequence to a second model at a second level of the system, wherein the first model of the first level generates a first digit, that corresponds to a class of the enzyme, and a second model of the second level is selected based on the class, and generates a second digit, that corresponds to a subclass of the enzyme, with the second model being one of six models of the second level, and wherein the first model is trained to determine the class and the six models are trained to determine the subclass.

12. The system of claim 11, wherein the first encoded sequence comprises a representation of a set of sequence-length dependent features of the enzyme and wherein the second encoded sequence comprises a representation of a set of sequence-length independent features of the enzyme.

13. The system of claim 11, wherein the first predicted characteristic is the first digit of an Enzyme Commission number associated with the enzyme and the second predicted characteristic is the second digit of the Enzyme Commission number associated with the enzyme.

14. The system of claim 11, wherein the system is further configured to:
generate a third predicted characteristic of the enzyme by applying the first encoded sequence and the second encoded sequence to a third model at a third level of the system; and
generate a fourth predicted characteristic of the enzyme by applying the first encoded sequence and the second encoded sequence to a fourth model at a fourth level of the system.

* * * * *